(12) United States Patent
Hakari et al.

(10) Patent No.: US 11,196,088 B2
(45) Date of Patent: Dec. 7, 2021

(54) LOCALIZED HIGH-SALT-CONCENTRATION ELECTROLYTES CONTAINING LONGER-SIDECHAIN GLYME-BASED SOLVENTS AND FLUORINATED DILUENTS, AND USES THEREOF

(71) Applicant: SES Holdings Pte. Ltd., Singapore (SG)

(72) Inventors: Takashi Hakari, Osaka (JP); Arunkumar Tiruvannamalai, Waltham, MA (US); Leran Zou, Arlington, MA (US); Mackenzie King, Essex, MA (US); Hong Gan, Miller Place, NY (US); Qichao Hu, Arlington, MA (US)

(73) Assignee: SES Holdings Pte. Ltd., Singapore (SG)

( * ) Notice: Subject to any disclaimer, the term of this patent is extended or adjusted under 35 U.S.C. 154(b) by 0 days.

(21) Appl. No.: 16/556,958

(22) Filed: Aug. 30, 2019

(65) Prior Publication Data

US 2020/0328475 A1  Oct. 15, 2020

Related U.S. Application Data

(60) Provisional application No. 62/832,676, filed on Apr. 11, 2019.

(51) Int. Cl.
*H01M 10/0569* (2010.01)
*H01M 10/052* (2010.01)
(Continued)

(52) U.S. Cl.
CPC ....... *H01M 10/0569* (2013.01); *C07C 317/28* (2013.01); *H01M 10/052* (2013.01);
(Continued)

(58) Field of Classification Search
CPC .......... H01M 10/0569; H01M 10/052; H01M 10/0567; H01M 10/0568
(Continued)

(56) References Cited

U.S. PATENT DOCUMENTS

| 6,168,884 B1 | 1/2001 | Neudecker et al. |
| 6,258,478 B1 | 7/2001 | Kim |

(Continued)

FOREIGN PATENT DOCUMENTS

| EP | 3118917 B1 | 1/2017 |
| JP | 2008218387 A * | 9/2008 |

(Continued)

OTHER PUBLICATIONS

Aurbach et al., "Prototype Systems for Rechargeable Magnesium Batteries," Nature, vol. 407 (6805), pp. 724-727 (2000).
(Continued)

*Primary Examiner* — Sean P Cullen
(74) *Attorney, Agent, or Firm* — Downs Rachlin Martin PLLC

(57) ABSTRACT

Localized high-salt-concentration electrolytes each containing a salt, a glyme as a solvent, and a fluorinated diluent. In some embodiments, the glyme has a chemical formula $R_1-(O-CH_2-CH_2)_n-O-R_2$, wherein n=1 to 4 and at least one of $R_1$ and $R_2$ is a hydrocarbon sidechain having at least 2 carbon atoms and wherein the salt is soluble in the glyme. In some embodiments, the fluorinated diluent is selected from the group consisting of a fluorinated glyme and a fluorinated ether. In some embodiments, the salt includes an alkali-metal salt. In some embodiments, the salt includes an alkali-earth-metal salt. The salt may include a perfluorinated sulfonimide salt. Electrochemical devices that include localized high-salt-concentration electrolytes of the present disclosure are also disclosed.

29 Claims, 3 Drawing Sheets

(51) Int. Cl.
*H01M 10/0568* (2010.01)
*C07C 317/28* (2006.01)
*H01M 10/0567* (2010.01)

(52) U.S. Cl.
CPC ... *H01M 10/0567* (2013.01); *H01M 10/0568* (2013.01); *H01M 2300/0028* (2013.01)

(58) Field of Classification Search
USPC .................................................. 429/199, 341
See application file for complete search history.

(56) References Cited

U.S. PATENT DOCUMENTS

| | | | |
|---|---|---|---|
| 6,402,795 B1 | 6/2002 | Chu et al. | |
| 6,706,447 B2 | 3/2004 | Gao et al. | |
| 7,776,465 B1 | 8/2010 | Hatazawa et al. | |
| 7,883,797 B2 | 2/2011 | Kishi et al. | |
| 8,460,808 B2 | 6/2013 | Toia et al. | |
| 8,715,865 B2 | 5/2014 | Xu et al. | |
| 8,834,180 B2 | 9/2014 | Woo et al. | |
| 8,865,350 B2 | 10/2014 | Yamada et al. | |
| 9,114,382 B2 | 8/2015 | Visconti et al. | |
| 9,190,696 B2 | 11/2015 | He et al. | |
| 9,887,415 B2 | 2/2018 | Fischer et al. | |
| 2007/0231707 A1 | 10/2007 | Abe et al. | |
| 2009/0023074 A1* | 1/2009 | Matsui ............. | H01M 10/0569 429/326 |
| 2009/0035662 A1 | 2/2009 | Scott et al. | |
| 2010/0227225 A1* | 9/2010 | Segawa ............. | H01M 10/052 429/324 |
| 2011/0123872 A1* | 5/2011 | Koh .................. | H01M 10/052 429/330 |
| 2012/0214073 A1* | 8/2012 | Iwaya ............... | H01M 10/0525 429/338 |
| 2013/0059178 A1 | 3/2013 | Ihara et al. | |
| 2013/0108932 A1* | 5/2013 | Onozaki ........... | H01M 10/0525 429/338 |
| 2013/0171514 A1 | 7/2013 | Mio et al. | |
| 2016/0006081 A1 | 1/2016 | Eaglesham et al. | |
| 2016/0172660 A1 | 6/2016 | Fischer | |
| 2016/0172661 A1 | 6/2016 | Fischer et al. | |
| 2016/0197376 A1 | 7/2016 | Koshiba et al. | |
| 2016/0233549 A1 | 8/2016 | Tiruvannamalai et al. | |
| 2016/0261000 A1 | 9/2016 | Zhang et al. | |
| 2016/0344063 A1* | 11/2016 | Chang .............. | H01M 10/0569 |
| 2017/0033406 A1 | 2/2017 | Zhang et al. | |
| 2017/0309960 A1 | 10/2017 | Lim | |
| 2018/0102531 A1 | 4/2018 | Fischer et al. | |
| 2018/0102532 A1 | 4/2018 | Fischer et al. | |
| 2018/0251681 A1 | 9/2018 | Zhang et al. | |
| 2018/0254524 A1 | 9/2018 | Zhang et al. | |
| 2019/0036179 A1 | 1/2019 | Downie et al. | |
| 2019/0036180 A1 | 1/2019 | Downie et al. | |
| 2019/0198932 A1* | 6/2019 | Newhouse ........ | H01M 10/0569 |
| 2019/0198933 A1 | 6/2019 | Newhouse et al. | |

FOREIGN PATENT DOCUMENTS

| | | |
|---|---|---|
| JP | 2008218387 A | 9/2008 |
| WO | 2015033619 | 12/2015 |

OTHER PUBLICATIONS

Aurbach et al., "Nonaqueous Magnesium Electrochemistry and its Application in Secondary Batteries," The Chemical Record, vol. 3, pp. 61-73 (2003).
Brandt, "Historical Development of Secondary Lithium Batteries," Solid State Ionics, vol. 69 (3-4), pp. 173-183 (1994).
Chalasani et al. "Methylene Ethylene Carbonate: Novel Additive to Improve the High Temperature Performance of Lithium Ion Batteries," Journal of Power of Sources, vol. 208, pp. 67-73 (2012).
Dahn, "Electrically Rechargeable Metal-Air Batteries Compared to Advanced Lithium-Ion Batteries," Presented at IBM Almadan Institute (2009).
Harry et al., "Detection of Subsurface Structures Underneath Dendrites Formed on Cycled Lithium Metal Electrodes," Nature Materials, vol. 13, pp. 69-73 (2014).
Gallagher et al., "Manufacturing Costs of Batteries for Electric Vehicles" Lithium-Ion Batteries: Advances and Applications, Chapter 6, pp. 97-126 (2014).
Li et al., "A Review of Lithium Deposition in Lithium-Ion and Lithium Metal Secondary Batteries," Journal of Power of Sources, vol. 254, pp. 168-182 (2014).
Liu et al., "Rechargeable Mg-Ion Batteries Based on WSe2 Nanowire Cathodes" ACS Nano, vol. 7(9), pp. 8051-8058 (2013).
Matsui, "Study on Electrochemically Deposited Mg Metal," Journal of Power Sources, vol. 196(16), pp. 7048-7055 (2011).
Mikhaylik, "Protection of Li Anodes Using Dual Phase Electrolytes," Sion Power, DoE EERE Report, 8 pages (2011).
Nguyen et al., "Improved Cycling Performance of SI Nanoparticle Anodes via Incorporation of Methylene Ethylene Carbonate," Electrochemistry Communications, vol. 66, pp. 71-74 (2016).
Park et al., "A Highly Reversible Lithium Metal Anode," Nature Scientific Reports, vol. 4, Report No. 3815, 8 pages (2014).
Von Sacken et al. "Comparative Thermal Stability of Carbon Intercalation Anodes and Lithium Metal Anodes for Rechargeable Lithium Batteries," Journal of Power Sources, vol. 54(2), pp. 240-245 (1995).
Vaughey et al. "Lithium Metal Anodes," Annual Merit Review, DOE Vehicle Technologies Program, 31 pages (2009).
Zheng et al., "Magnesium Cobalt Silicate Materials for Reversible Magnesium Ion Storage," Electrochimica Acta, vol. 66, pp. 75-81 (2012).
International Search Report and Written Opinion dated Mar. 18, 2019, in Appl. No. PCT/US2018/066557.

* cited by examiner

LOCALIZED HIGH-SALT-CONCENTRATION ELECTROLYTES CONTAINING LONGER-SIDECHAIN GLYME-BASED SOLVENTS AND FLUORINATED DILUENTS, AND USES THEREOF

RELATED APPLICATION DATA

This application claims the benefit of priority of U.S. Provisional Patent Application Ser. No. 62/832,676, filed Apr. 11, 2019, and titled "HIGH SALT CONCENTRATION ELECTROLYTES WITH DILUENTS FOR SECONDARY LITHIUM BATTERIES", which is incorporated by reference herein in its entirety.

FIELD OF THE INVENTION

The present invention generally relates to the field of electrolytes for electrochemical devices. In particular, the present invention is directed to localized high-salt-concentration electrolytes containing longer-sidechain glyme-based solvents and fluorinated diluents, and uses thereof.

BACKGROUND

High-salt-concentration electrolytes are known to enhance cycle life in rechargeable, or secondary, batteries having lithium-metal anodes. In particular, electrolytes with greater than 2 molar (M) of LiFSI or LiTFSI salt dissolved in glyme-based solvents are known to enhance charge-discharge cycle-life performance in batteries having lithium-metal anodes. In conventional electrolytes having ~1M lithium salt concentration, the solvent molecules undergo reduction at the surface of the lithium-metal anode to form a solid-electrolyte interphase (SEI) (passivation) layer. In a high-salt-concentration lithium-based electrolyte, most of the solvent molecules will remain associated with the solvated $Li^+$ ions and are not available to form the SEI layer. In the absence of free solvent molecules, a more compact and stable SEI is formed on the lithium anode's surface by the fluorinated anion of the lithium salt, which leads to higher lithium plating/stripping coulombic efficiency and enhanced cycle life performance of the battery.

High-salt-concentration electrolytes, however, have several disadvantages, such as low conductivity, high viscosity, and the consequent poor wetting of electrodes and separator, resulting in lower charge-discharge rates (C-rates) than those typically used in conventional secondary batteries. High-salt-concentration electrolytes also incur higher production cost due to their high salt content, with the salt typically being the most expensive constituent of the electrolyte. Diluting high-salt-concentration electrolytes with excess solvent creates more free-solvent molecules that react with and consume the lithium-metal anode, thus reducing the coulombic efficiency and cycle life of the battery.

Furthermore, to offset the high viscosity caused by high salt concentration, these electrolytes often make use of low-boiling-point DME (1,2-Dimethoxyethane or monoglyme or Ethylene glycol dimethyl ether) as the solvent. Use of low boiling solvents such as DME typically leads to significant gas generation in cells exposed to high ambient temperature while in a charged state.

SUMMARY OF THE DISCLOSURE

In an implementation, the present disclosure is directed to an electrolyte that includes a salt; a solvent comprising a glyme of the formula $R_1$—(O—$CH_2$—$CH_2$)$_n$—O—$R_2$, wherein n=1 to 4 and at least one of $R_1$ and $R_2$ is a hydrocarbon sidechain having at least 2 carbon atoms, wherein the salt is soluble in the solvent; and a diluent selected from the group consisting of a fluorinated glyme and a fluorinated ether.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1A:
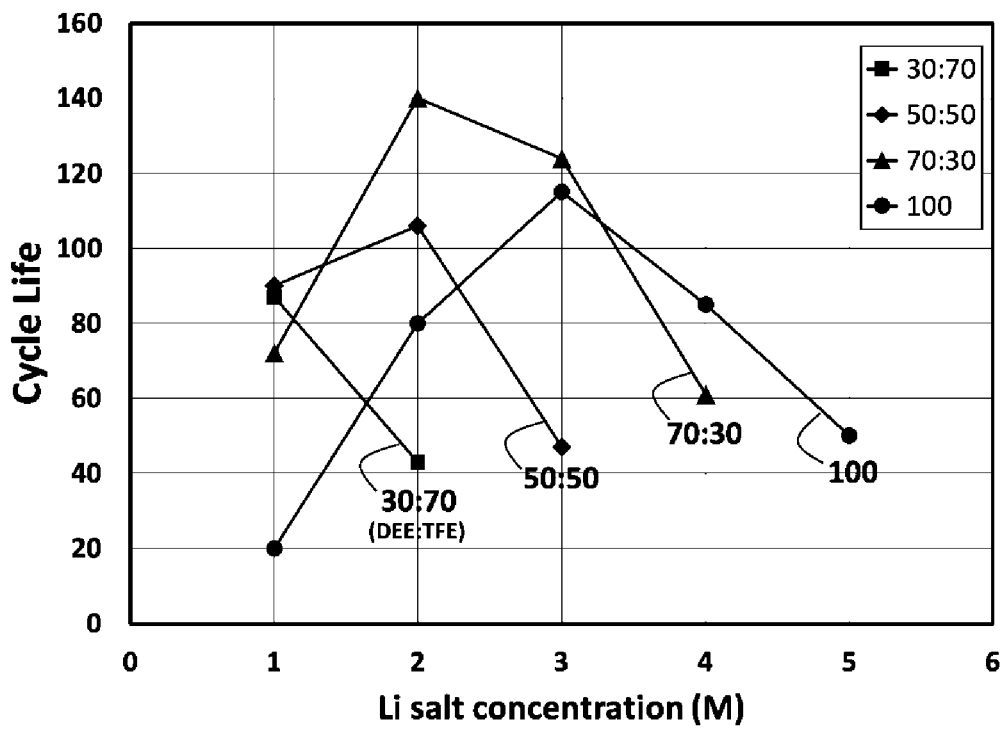
FIG. 1A is a graph of cycle life versus lithium-salt concentration for several example localized high-salt-concentration (LHSC) electrolytes of the present disclosure, each composed of lithium bis(fluorosulfonyl)imide salt (LiFSI), 1,2-11diethoxyethane (DEE), and 1,2-(1,1,2,2-tetrafluoroethoxy)-ethane (TFE) and with differing DEE:TFE volumetric percentage ratios.

In some aspects, the present disclosure is directed to localized high-salt-concentration (LHSC) electrolytes made using longer-sidechain glymes and fluorinated diluents. LHSC electrolytes made in accordance with this disclosure may have a high concentration of lithium salt, such as LiFSI or LiTFSI, for example, dissolved in a longer-sidechain glyme-based solvent, such as DEE (1,2-diethoxyethane or ethylene glyme), having one or more sidechains that extend the length of the molecular structure of the base glyme, whether it be a monoglyme or polyglyme. In the context of a monoglyme, the base glyme is DME (1,2-dimethoxyethane). As used herein and in the appended claims, the term "longer-sidechain glyme-based solvent" denotes a glyme-based solvent having an additional hydrocarbon molecular structure attached to at least one end of the glyme molecular structure. Examples of longer-sidechain glyme-based solvents are described in detail below. LHSC electrolytes made in accordance with the present disclosure may also include a fluorinated hydrocarbon, such as a fluorinated glyme or fluorinated ether, added as a diluent to overcome disadvantages usually associated with high-salt-concentration electrolytes.

The fluorinated diluent is typically miscible with the longer-sidechain glyme-based solvent used in the LHSC electrolyte, but it is designed or selected to have much lower lithium-salt solubility relative to glyme-based solvents by virtue of its low polarity. As a result, the solvent molecules of the longer-sidechain glyme-based solvent and the lithium ions from the lithium-based salt will remain associated with one another even after the addition of diluent and thus retain the advantages of a high-salt-concentration electrolyte. Moreover, the addition of the fluorinated diluent decreases the overall viscosity and helps improve the conductivity and wetting properties of the LHSC electrolyte, without increasing the amount of free solvent molecules in the electrolyte. In turn, this allows use of higher charge-discharge rates, for example, charge-discharge rates typically used in conventional secondary batteries such as lithium-ion batteries, without sacrificing the high coulombic efficiency and cycle life of the battery. In addition, as the diluent is fluorinated, it may also help form a more compact and stable solid-electrolyte interphase (SEI) on, for example, the lithium-metal surface of the anode of a lithium-metal secondary battery, in a manner analogous to the fluorinated anion of the lithium salt.

Furthermore, the fluorinated diluent also allows the use of the more stable longer-sidechain glyme-based solvents (such as DEE (1,2-diethoxyethane or ethylene glycol diethyl ether), DPE (1,2-dipropoxyethane or ethylene glycol dipropyl ether), DBE (1,2-dibutoxyethane or ethylene glycol dibutyl ether), diethylene glycol diethyl ether, diethylene glycol dipropyl ether, triethylene glycol dibutyl ether, triethylene glycol diethyl ether, triethylene glycol dipropyl ether, triethylene glycol dibutyl ether, tetraethylene glycol diethyl ether, tetraethylene glycol dipropyl ether, tetraethylene glycol dibutyl, etc.,) that, by themselves, are relatively more viscous than DME in making high-salt-concentration electrolyte. Use of the more-stable longer-sidechain glyme-based solvents of the present disclosure, in turn, prevents or decreases gas generated in charged electrochemical cells exposed to high ambient temperatures. The decomposition products of the longer-sidechain glyme-based solvents typically would be relatively larger molecules having higher boiling points (relative to DME, for example) that may tend to dissolve more into the LHSC electrolyte instead of generating gas inside the cell. In addition, having one or more longer sidechains increases the molar volume of the glyme-based solvent, which in turn decreases the amount of salt required per unit volume of the LHSC electrolyte (mole concentration or molarity) to maintain association between the $Li^+$ ions and solvent molecules and, consequently, lowers the volumetric cost of producing the LHSC electrolyte.

In another aspect, the present disclosure is directed to uses of lithium-based LHSC electrolytes made in accordance with the present disclosure. For example, these LHSC electrolytes can be used in any suitable lithium-based electrochemical device, such as a battery or supercapacitor. Lithium-based LHSC electrolytes made in accordance with the present disclosure can provide, for example, greater charge-discharge cycle life and reduced gas production to the electrochemical devices, while providing desirable wetting and SEI-formation characteristics and allowing for favorable C rates, among other things.

Details of the foregoing and other aspects of the present disclosure are described below.

Throughout the present disclosure, the term "about" when used with a corresponding numeric value refers to ±20% of the numeric value, typically ±10% of the numeric value, often ±5% of the numeric value, and most often ±2% of the numeric value. In some embodiments, the term "about" can be taken as exactly indicating the actual numerical value.

Localized High-Salt-Concentration Electrolytes

Example Longer-Sidechain Glyme-Based Solvents

Structure 1, below, shows the general molecular structure of a longer-sidechain glyme $R_1$—(O—$CH_2$—$CH_2$)$_n$—O—$R_2$ that can be used in an LHSC electrolyte made in accordance with the present disclosure. Longer-sidechain glymes of this disclosure will have at least one sidechain structure ($R_1$ or $R_2$) that has 2 to 6 carbon atoms. The sidechains can be linear, branched, cyclic, either partially or completely saturated. The sidechains can have the same or different molecular structure (i.e., $R_1$=$R_2$ or $R_1$≠$R_2$). Having a methyl (—$CH_2$) sidechain with one carbon atom on both sides (i.e., for each of $R_1$ and $R_2$) will yield DME, which, as noted above, is conventionally used as solvent in some high-concentration electrolytes. As also noted above, DME has some distinct drawbacks in some electrochemical cell applications, such as secondary lithium-metal batteries.

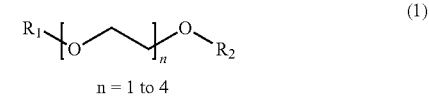

(1)

n = 1 to 4

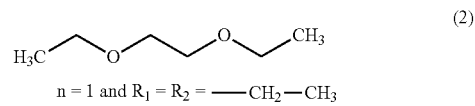

(2)

n = 1 and $R_1$ = $R_2$ = —$CH_2$—$CH_3$

For the sake of illustration, Structure 2, above, is the molecular structure of DEE (1,2-diethoxyethane, or ethylene glyme, or CH3-CH2—O—CH2—CH2—O—CH2—CH3), wherein the sidechains $R_1$ and R2 are both ethyl (—CH2-CH3) groups. DEE is utilized below as an example longer-sidechain glyme-based solvent of the present disclosure. However, those skilled in the art will readily appreciate that DEE is merely an example and is not intended to limit the selection of another longer-sidechain glyme-based solvent, such as a solvent having the foregoing generalized molecular structure of Structure 1, above, for an LHSC electrolyte made in accordance with the present disclosure.

Example Fluorinated Diluents

In some embodiments, a high-salt-concentration electrolyte of the present disclosure may be made using a fluorinated hydrocarbon, such as a fluorinated glyme or a fluorinated ether. Structure 3, below, illustrates a fluorinated glyme in the form of 1,241,1,2,2-tetrafluoroethoxy)-ethane (TFE).

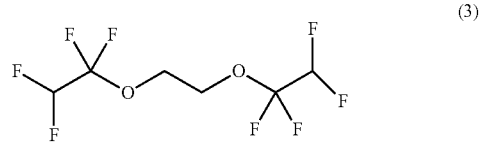 [SMILES: FC(F)C(F)(F)OCCOC(F)(F)C(F)F]

(3)

TFE is used as an example fluorinated diluent herein, particularly in combination with the DEE longer-sidechain glyme-based solvent addressed in the section above. It is noted that the backbone structure of TFE is similar to the backbone of DEE. Consequently, TFE and DEE are more likely to be miscible with one another. The presence of 8 fluorine atoms in the TFE molecule makes it less polar such that the lithium salt will be less soluble, for example, about 10 times or more less soluble, in TFE. Consequently, when selecting a diluent and solvent in accordance with the present disclosure it can be desirable to select a diluent and solvent having similar backbone structures.

Two additional examples of fluorinated diluents are illustrated in Structures 4 and 5, below.

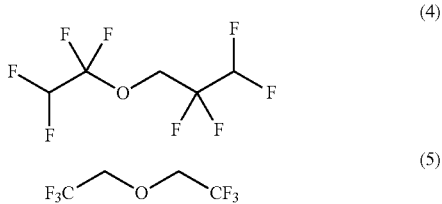

(4)

(5)

The fluorinated diluent of Structure 4 is the fluorinated ether 1,1,2,2-tetrafluoroethyl-2,2,3,3-tetrafluoropropyl ether (TTE), and the fluorinated diluent of Structure 5 is the fluorinated ether bis(2,2,2-trifluoroethyl) ether (BTFE). The foregoing are but a few examples of fluorinated glymes and fluorinated ethers suitable for use in a high-salt-concentration electrolyte according to the present disclosure. In some embodiments, diluents of the present disclosure includes suitable hydrocarbon molecules having at least one oxygen (—O—) linkage and at least one fluorine (—F) substitution.

Example Li-Based Salts

A number of lithium-based salts may be used to make a high-salt-concentration electrolyte of the present disclosure. For example, in some embodiments it is desirable to use lithium bis(fluorosulfonyl)imide (LiFSI), the molecular structure of which is illustrated in Structure 6, below.

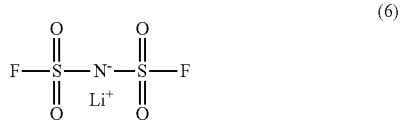

(6)

In some embodiments, it is desirable to use a lithium-based salt having the general formula $(Li^+)(CF_3—(CF_2)_n—SO_2—N^-—SO_2—(CF_2)n—CF_3)$, wherein $n \geq 0$. The molecular structure of this general formula is illustrated in Structure 7, below. Structure 8, also below, illustrates the case in which n=0, which is lithium bis(trifluoromethanesulfonyl)imide (LiTFSI).

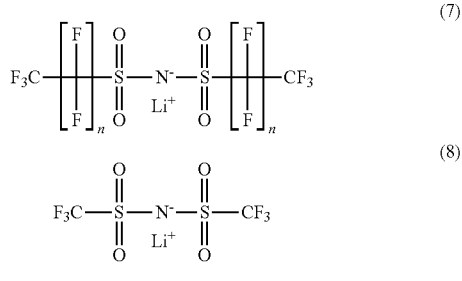

(7)

(8)

It is noted that while lithium perfluorinated sulfonimide salts are exemplified herein, teachings of the present disclosure may be implemented with other salts, such as alkali-metal-based salts and alkali-earth-metal-based salts, such as perfluorinated sulfonimide salts based on sodium or magnesium, to name a couple. In addition, salts commonly used in lithium-ion batteries, such as $LiPF_6$, $LiAsF_6$, $LiBF_4$, LiBOB, Li-triflate, etc., can be used in high-salt-concentration electrolytes made in accordance with the present disclosure.

Broadly, an electrolyte made in accordance with the present disclosure may have a salt concentration in a range of about 0.1M to about 10M, while in some embodiments the salt concentration may be desired in a range of about 1M to about 5M, and in other embodiments the salt concentration may be desired in a range of about 2M to about 3M. In some embodiments, the solvent:diluent ratio of an electrolyte made in accordance with the present disclosure may by in a range of about 10:90 to 100:0. In some embodiments, the solvent:diluent ratio may be desired to be in a range of about 40:60 to about 90:10, and in other embodiments the solvent:diluent ratio may be desired to be in a range of about 60:40 to about 80:20.

Example High-Salt-Concentration Electrolytes and Test Data

The following example LHSC electrolytes utilize LiFSI as the salt, DEE as the longer-sidechain glyme-based solvent, and TFE as the fluorinated diluent. A number of LHSC electrolyte compositions were made with various concentrations of the LiFSI salt (1M to 5M) and with differing volumetric ratios of DEE:TFE (30% to 100%), and these compositions were tested for cycle life and gas formation.

Cycle life was tested using identical pouch-type secondary battery cells built using nickel-manganese-cobalt (NMC) cathodes, lithium-metal anodes, and microporous polyolefin-based separators. During testing, the cells, containing corresponding ones of the LHSC electrolyte compositions, were cycled between 3V to 4.3V at a C/3-C/2 charge-discharge rate. The Table below shows the charge-discharge cycle life attained (at 80% capacity retention) in lithium cells made with various LiFSI+DEE+TFE LHSC electrolyte compositions of this disclosure. In the below Table, the cycle lives for DEE:TFE ratios at which the LiFSI salt of the corresponding concentration were not completely soluble are denoted by a "-". In general, with higher diluent (here, TFE) amounts, less LiFSI salt could be dissolved in the LHSC electrolyte, since TFE is a fluorinated glyme having low polarity and salt solubility.

TABLE

| LiFSI conc. | Cycle Life DEE:TFE volume ratio | | | |
|---|---|---|---|---|
| | 30:70 | 50:50 | 70:30 | 100:0 |
| 1M | 87 | 90 | 72 | 20 |
| 2M | 43 | 106 | 140 | 80 |
| 3M | — | 47 | 124 | 115 |
| 4M | — | — | 61 | 85 |
| 5M | — | — | — | 50 |

Figure 1B:
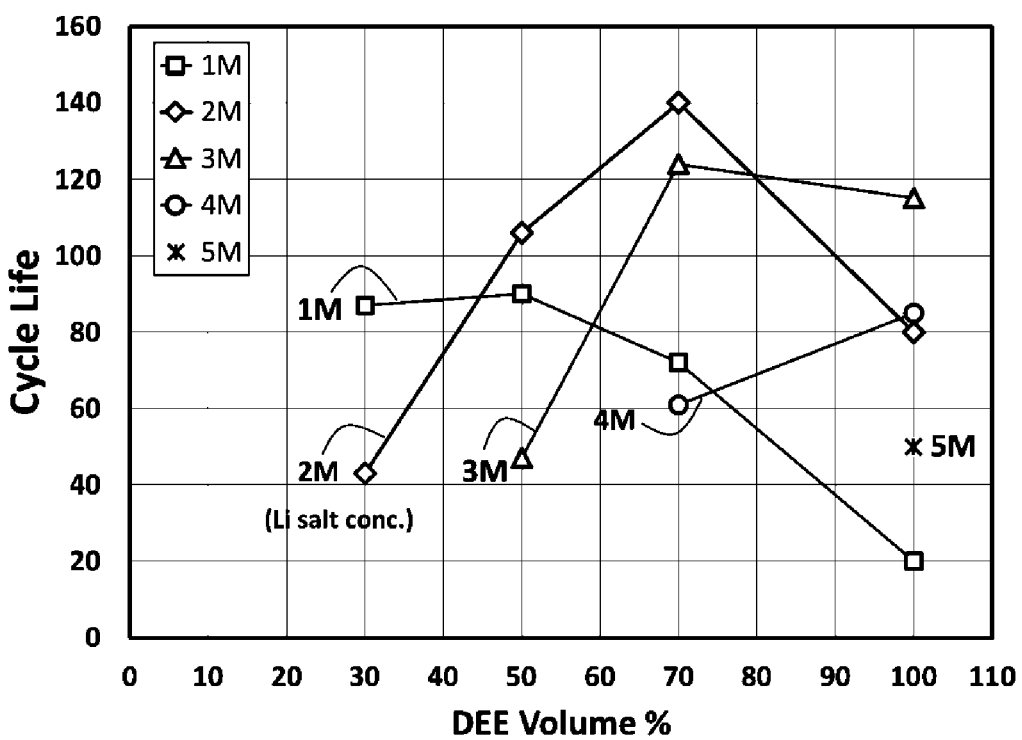
FIG. 1B is a graph of cycle life versus DEE volume percentage for differing salt (LiFSI) concentrations of the LHSC electrolytes of FIG. 1A.

Turning now to the accompanying drawings, FIG. 1A shows the variation in cycle life with respect to the lithium salt concentration of the various LiFSI+DEE+TFE LHSC electrolyte compositions noted above, and FIG. 1B shows the variation in cycle life with respect to DEE volume percentage for those electrolyte compositions. As seen in FIGS. 1A and 1B and in general, cycle life of the cells tends to be high near 2M or 3M lithium salt concentration and near 70:30 DEE:TFE volume ratio.

Figure 2:
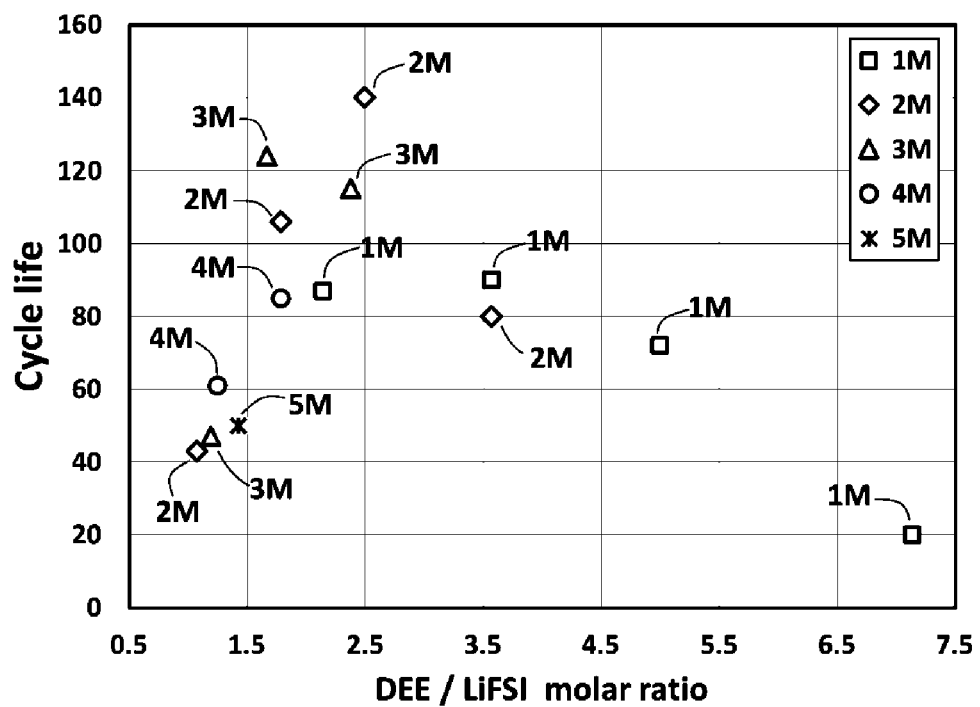
FIG. 2 is a graph of cycle life versus DEE/LiFSI (solvent/salt) molar ratio in the various LHSC electrolytes of FIGS. 1A and 1B.

FIG. 2 shows the variation in cycle life with respect to the solvent/salt (DEE/LiFSI) molar ratio in the LHSC electrolyte, regardless of the diluent (TFE) amount. It has been known that a 2:1 solvent/salt molar ratio in a conventional high-salt-concentration lithium-based electrolyte is optimal for cycle-life performance of a cell, since each lithium ion associates with an average of two DME molecules in the electrolyte. In this regard, FIG. 2 also indicates enhanced cycle life for cells with LHSC electrolytes of this disclosure having solvent:salt (DEE/LiFSI) molar ratio about 2:1. This corroborates the fact that the solvent (DEE) molecules and solvated lithium ions remain associated even after the addition of the TFE diluent, thus retaining the advantages of a high-salt-concentration electrolyte, while improving the charging-discharging rate performance of the cell. In some embodiments, the solvent:salt molar ratio is in a range of about 1:1 to about 4:1. In some embodiments, the solvent:salt ratio is in a range of about 1.5:1 to about 3:1. A solvent:salt molar ratio of 2:1 for DEE/LiF SI roughly corresponds to about 3.6 moles of LiFSI salt for every liter of DEE solvent in the electrolyte. When the solvent: salt molar ratio is 2:1, those skilled in the art will understand that the (solvent+diluent):salt molar ratio will be greater than 2:1. This is so for the simple reason that 2:1 is the molar ratio for the solvent alone, whereas the addition of diluent in the combination of the solvent+diluent increases the number of moles on the left-hand side of the molar ratio. For example, for the 70:30 DEE/TFE (solvent/diluent) volume ratio in the preceding paragraph with LiFSI as the salt, when the solvent:salt molar ratio is 2:1, the (solvent+diluent):salt molar ratio is 2.7:1. As other examples utilizing LiFSI, DEE, TFE, and a solvent:salt molar ratio of 2:1: at a 50:50 solvent:diluent volume ratio, the (solvent+diluent):salt molar ratio is 3.6:1, at a 60:40 solvent:diluent volume ratio, the (solvent+diluent):salt molar ratio is 3.1:1, at an 80:20 solvent:diluent volume ratio, the (solvent+diluent):salt molar ratio is 2.4:1, and at a 90:10 solvent: diluent volume ratio, the (solvent+diluent):salt molar ratio is 2.2:1.

Figure 3A:
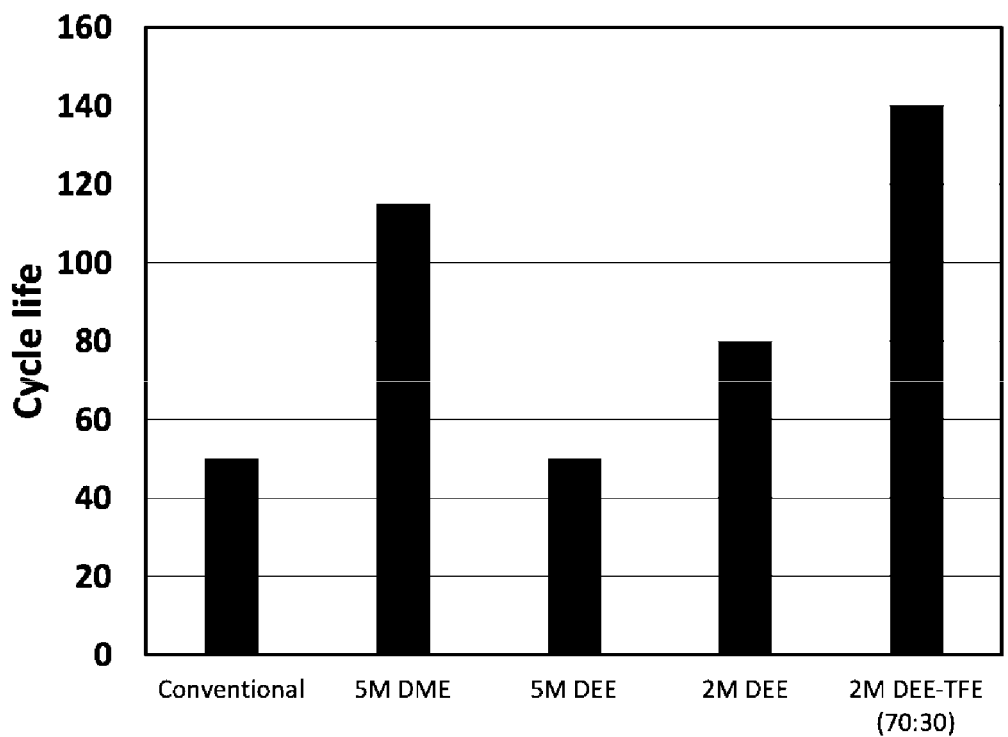
FIG. 3A is a chart showing cycle life for a number of differing electrolytes, including a 2M LiFSI+DEE+TFE LHSC electrolyte of the present disclosure having a 70:30 DEE:TFE volumetric percentage ratio.

FIG. 3A compares the cycle life attained with various electrolytes in cells that were cycled between 3 to 4.3V at C/3-C/2 charge-discharge rate. The LHSC electrolyte of this disclosure having a longer-sidechain glyme-based solvent and a fluorinated glyme diluent (the LHSC electrolyte labeled "2M DEE:TFE (70:30)" in FIG. 3A) shows higher cycle-life performance than "Conventional" carbonate-based electrolytes and high-salt-concentration electrolytes (labeled "5M DME", "5M DEE", and "2M DEE" in FIG. 3A) containing no diluent. In this context, "Conventional" carbonate-based electrolytes include electrolytes using LiFSI, a cyclic carbonate solvent (e.g., EC (Ethylene Carbonate) or FEC (Fluorinated Ethylene Carbonate)), and optionally a linear carbonate diluent (e.g., EMC (Ethyl Methyl Carbonate). In an example, a "Conventional" electrolyte in this context may be a 1M to 3M LiFSI solution in EC, and in another example, a "Conventional" electrolyte in this context may be a 1M to 3M LiFSI solution in FEC:EMC in a 2:8 volumetric ratio.

Figure 3B:
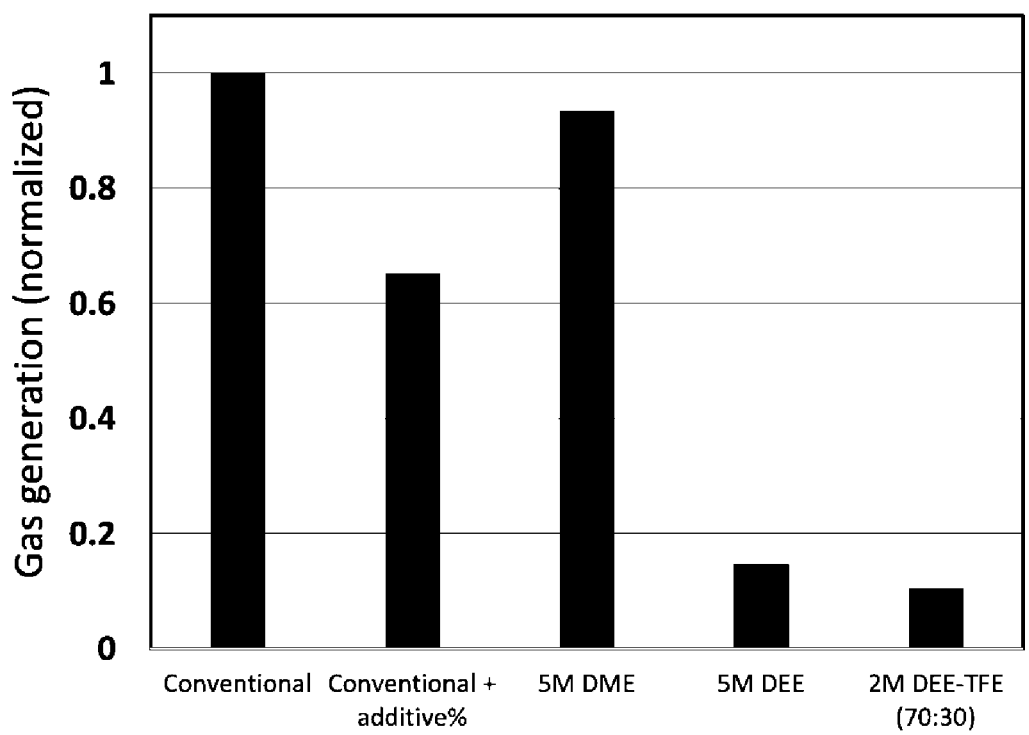
FIG. 3B is a chart showing normalized gas generation for the electrolytes of FIG. 3A.

In addition, the use of more-stable longer-sidechain glyme-based solvent, such as DEE, would decrease the amount of gas generated in charged cells exposed to high ambient temperatures. FIG. 3B shows the relative amounts of gas generated by various electrolytes in fully charged (state-of-charge (SOC) 100) pouch cells (described above) exposed for a week to 45° C. ambient temperature. Carbonate-solvent-based electrolytes conventionally used in lithium-ion batteries produced the most amount of gas in the cell. Gas-suppressing additives in the carbonate electrolyte did not yield any significant reduction in gas volume. The high-salt-concentration electrolyte (labeled "5M DME" in FIG. 3B) made with monoglyme solvent also showed gas generation similar to that of the carbonate-based electrolytes. The use of longer-sidechain glymes-based solvent, such as DEE, in high-salt-concentration electrolyte result in significant reduction in gas volume (labeled "5M DEE" in FIG. 3B). Furthermore, the LHSC electrolyte composition of this disclosure in this example (labeled "2M LiFSI in DEE:TFE (70:30)" in FIG. 3B) having enhanced cycle-life performance, also shows a significantly lower gas generation.

The lower gas generation along with enhanced cycle-life performance at higher charge-discharge rates makes the LHSC electrolytes of the present disclosure, which contain a longer-sidechain glyme-based solvent and a fluorinated-glyme or fluorinated-ether diluent, target electrolytes for lithium-metal electrochemical devices, such as secondary batteries and supercapacitors.

Example Uses of LHSC Electrolytes of the Present Disclosure

Figure 4:
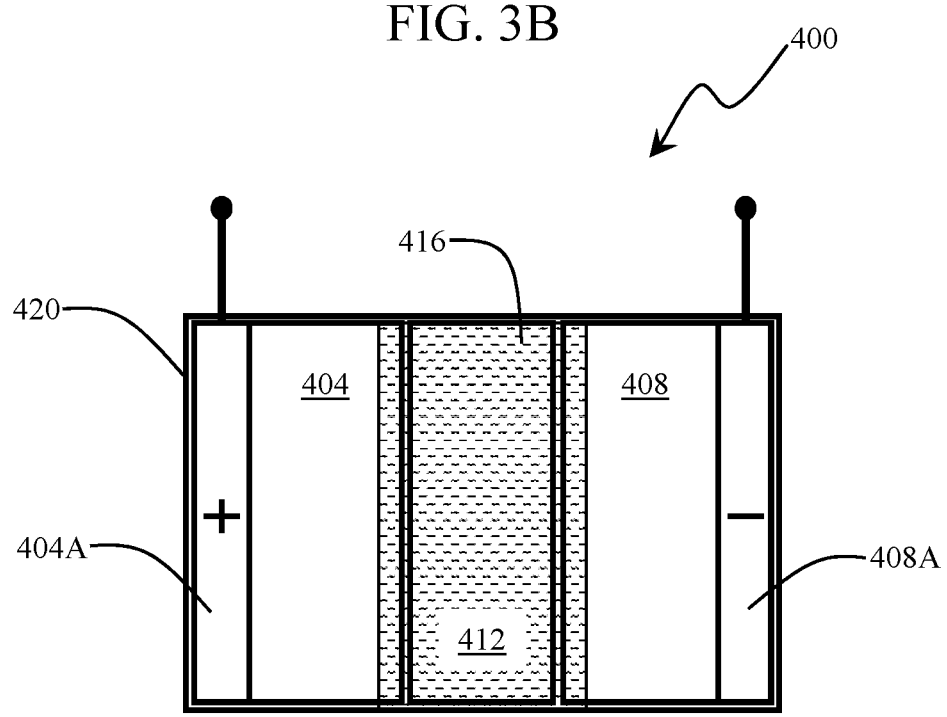
FIG. 4 is a high-level diagram illustrating an electrochemical device made in accordance with aspects of the present disclosure.

As mentioned above, an LHSC electrolyte of the present disclosure may be used as an electrolyte for an electrochemical device, among other things. FIG. 4 illustrates an electrochemical device 400 made in accordance with aspects of the present disclosure. Those skilled in the art will readily appreciate that the electrochemical device 400 can be, for example, a battery or a supercapacitor. In addition, those skilled in the art will readily understand that FIG. 4 illustrates only some basic functional components of the electrochemical device 400 and that a real-world instantiation of the electrochemical device, such as a secondary battery or a supercapacitor, will typically be embodied using either a wound construction or a stacked construction. Further, those skilled in the art will understand that the electrochemical device 400 will include other components, such as electrical terminals, seal(s), thermal shutdown layer(s), and/or vent(s), among other things, that, for ease of illustration, are not shown in FIG. 4.

In this example, the electrochemical device 400 includes spaced-apart positive and negative electrodes 404, 408, respectively, and a pair of corresponding respective current collectors 404A, 408A. A porous dielectric separator 412 is located between the positive and negative electrodes 404, 408 to electrically separate the positive and negative electrodes but to allow ions of an LHSC electrolyte 416 made in accordance with the present disclosure to flow therethrough. The porous dielectric separator 412 and/or one, the other, or both of the positive and negative electrodes 404, 408, if porous, is/are impregnated with the LHSC electrolyte 416. In FIG. 4, both the positive and negative electrodes 404, 408 are illustrated as being porous by way of the LHSC electrolyte 416 being illustrated as extending into them. In some embodiments, such as certain embodiments of lithium-metal secondary batteries having solid-type lithium-metal negative electrodes, one, the other, or both of the positive and negative electrodes 404, 408 need not be porous. As described above, benefits of using an LHSC electrolyte of the present disclosure for LHSC electrolyte 416 can include the facts that less salt is needed than in DME-based electrolytes because of the larger molecules of the longer-sidechain glyme-based solvent and the fluorinated diluent, less gas is produced at higher temperatures, cycle-life performance is enhanced, higher coulombic efficiency are possible, and higher charging-discharging rates are possible. Examples of LHSC electrolytes suitable for use as the LHSC electrolyte 416 are described above. In some deployments, LHSC electrolytes of the present disclosure are particularly suited for use in cyclable lithium-metal based electrochemical devices, such as secondary lithium-metal batteries. As disclosed herein, various compositions of LHSC electrolytes of the present disclosure can yield cycle-life performance superior to other types of electrolytes. The electrochemical device 400 includes a container 420 that contains the current collectors 404A, 408A, the positive and negative electrodes 404, 408, the porous dielectric separator 412, and the LHSC electrolyte 416.

As those skilled in the art will understand, depending upon the type and design of the electrochemical device, each of the positive and negative electrodes 404, 408 comprises a suitable material compatible with the alkali-metal ions and other constituents in the LHSC electrolyte 416. Each of the current collectors 404A, 408A may be made of any suitable electrically conducting material, such as copper or aluminum, or any combination thereof. The porous dielectric separator 412 may be made of any suitable porous dielectric material, such as a porous polymer, among others. Various battery and supercapacitor constructions that can be used for constructing the electrochemical device 400 of FIG. 4, are known in the art. If any of such known constructions is used, a novelty of electrochemical device 400 lies in the composition of the LHSC electrolyte 416.

In some aspects, the present disclosure is direct to an electrolyte comprising: a salt; a solvent comprising a glyme of the formula $R_1$—(O—$CH_2$—$CH_2$)$_n$—O—$R_2$, wherein n=1 to 4 and at least one of $R_1$ and $R_2$ is a hydrocarbon sidechain having at least 2 carbon atoms, wherein the salt is soluble in the solvent; and a diluent selected from the group consisting of a fluorinated glyme and a fluorinated ether.

In one or more embodiments of the electrolyte, the salt comprises an alkali-metal salt.

In one or more embodiments of the electrolyte, the salt comprises a perfluorinated sulfonimide salt.

In one or more embodiments of the electrolyte, the perfluorinated sulfonimide salt comprises a lithium-based perfluorinated sulfonimide salt.

In one or more embodiments of the electrolyte, the lithium-based perfluorinated sulfonimide salt comprises lithium bis(fluorosulfonyl)imide.

In one or more embodiments of the electrolyte, the salt comprises a lithium-based salt.

In one or more embodiments of the electrolyte, the salt has a concentration in the electrolyte in a range of about 0.1M to about 10M.

In one or more embodiments of the electrolyte, the salt has a concentration in the electrolyte in a range of about 1M to about 5M.

In one or more embodiments of the electrolyte, the salt has a concentration in the electrolyte in a range of about 2M to about 3M.

In one or more embodiments of the electrolyte, the electrolyte has a volumetric solvent:diluent percentage ratio of about 10:90 to about 100:0.

In one or more embodiments of the electrolyte, the electrolyte has a volumetric solvent:diluent percentage ratio of about 40:60 to about 90:10.

In one or more embodiments of the electrolyte, the electrolyte has a volumetric solvent:diluent percentage ratio of about 60:40 to about 80:20.

In one or more embodiments of the electrolyte, the electrolyte has a solvent:salt molar ratio in a range of about 1:1 to about 4:1.

In one or more embodiments of the electrolyte, the electrolyte has a solvent:salt molar ratio in a range of about 1.5:1 to about 3:1.

In one or more embodiments of the electrolyte, the electrolyte has a solvent:salt molar ratio in a range of about 2:1.

In one or more embodiments of the electrolyte, $R_1$=$R_2$.

In one or more embodiments of the electrolyte, the hydrocarbon sidechain has 2 to 6 carbon atoms.

In one or more embodiments of the electrolyte, n=1 and each of $R_1$ and R2 is an ethyl group, as in 1,2-diethoxyethane (DEE).

In one or more embodiments of the electrolyte, the diluent comprises a fluorinated ether.

In one or more embodiments of the electrolyte, the diluent comprises a fluorinated glyme.

In one or more embodiments of the electrolyte, the fluorinated glyme is 1,2-(1,1,2,2-tetrafluoroethoxy)-ethane (TFE).

In one or more embodiments of the electrolyte, the salt comprises lithium bis(fluorosulfonyl)imide.

In one or more embodiments of the electrolyte, the concentration of the salt is at least 2M.

In one or more embodiments of the electrolyte, the solvent and the diluent are present in a solvent:diluent volumetric percentage ratio in which the solvent is at least 40% and the diluent is no more than 60%.

In one or more embodiments of the electrolyte, the solvent and the diluent are present in a solvent:diluent volumetric percentage ratio in which the solvent is at least 60% and the diluent is no more than 40%.

In one or more embodiments of the electrolyte, the concentration of the salt is at least 3M.

In one or more embodiments of the electrolyte, the solvent and the diluent are present in a solvent:diluent volumetric percentage ratio in which the solvent is at least 40% and the diluent is no more than 60%.

In one or more embodiments of the electrolyte, the solvent and the diluent are present in a solvent:diluent volumetric percentage ratio in which the solvent is at least 60% and the diluent is no more than 40%.

In one or more embodiments of the electrolyte, the salt comprises lithium bis(fluoro-sulfonyl)imide.

In one or more embodiments of the electrolyte, the salt is selected from the group consisting of lithium bis(fluorosulfonyl)imide and a salt of a molecular structure:

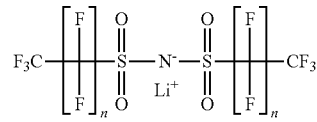

wherein n is equal to or greater than 0.

In some aspects, the present disclosure is directed to an electrochemical device, comprising: a positive electrode; a negative electrode spaced from the positive electrode; a porous dielectric separator located between the positive and negative electrodes; and the electrolyte according to any one of the foregoing electrolyte embodiments contained within at least the porous dielectric separator.

In one or more embodiments of the electrochemical device, the negative electrode comprises a lithium metal.

In one or more embodiments of the electrochemical device, the electrochemical device is a secondary battery and the negative electrode is a lithium metal electrode.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the Applications of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An electrolyte, consisting of:
a salt;
a solvent that is a glyme of the formula $R_1$—(O—$CH_2$—$CH_2$)$_n$—O—$R_2$, wherein n=1 to 4 and at least one of $R_1$ and $R_2$ is a hydrocarbon sidechain having at least 2 carbon atoms, wherein the salt is soluble in the solvent; and
a diluent selected from the group consisting of a fluorinated glyme and a fluorinated ether;
wherein:
the salt has a concentration in the electrolyte of about 0.2 M to less than 5 M;
the electrolyte has a (solvent+diluent):salt molar ratio in a range of greater than 2:1 to about 8:1; and
the electrolyte has a volumetric solvent:diluent percentage ratio of about 50:50 to about 90:10.

2. The electrolyte of claim 1, wherein the salt comprises a lithium-based salt.

3. The electrolyte of claim 1, wherein the concentration of the salt is in a range of about 1M to less than 5M.

4. The electrolyte of claim 1, wherein the concentration of the salt is in a range of about 2M to about 3M.

5. The electrolyte of claim 1, having a solvent:salt molar ratio in a range of about 2:1 to about 4:1.

6. The electrolyte of claim 1, having a solvent:salt molar ratio in a range of about 2:1 to about 3:1.

7. The electrolyte of claim 1, having a solvent:salt molar ratio is about 2:1.

8. The electrolyte of claim 1, wherein $R_1$=$R_2$.

9. The electrolyte of claim 1, wherein the hydrocarbon sidechain has 2 to 6 carbon atoms.

10. The electrolyte of claim 1, wherein the salt is selected from the group consisting of lithium bis(fluorosulfonyl) imide and a salt of a molecular structure:

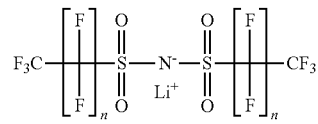

wherein n is equal to or greater than 0.

11. The electrolyte of claim 1, wherein the concentration of the salt is in a range of about 0.2M to about 4M.

12. The electrolyte of claim 1, wherein the volumetric solvent:diluent percentage ratio of the electrolyte is about 60:40 to about 80:20.

13. The electrolyte of claim 12, wherein the concentration of the salt is in a range of about 0.2M to about 4M.

14. The electrolyte of claim 1, wherein the concentration of the salt is at least 2M.

15. The electrolyte of claim 14, wherein, in the solvent: diluent volumetric percentage ratio, the solvent is at least 50% and the diluent is no more than 50%.

16. The electrolyte of claim 14, wherein, in the solvent: diluent volumetric percentage ratio, the solvent is at least 60% and the diluent is no more than 40%.

17. The electrolyte of claim 1, wherein n=1 and each of $R_1$ and $R_2$ is an ethyl group, as in 1,2-diethoxyethane (DEE).

18. The electrolyte of claim 17, wherein the diluent comprises a fluorinated ether.

19. The electrolyte of claim 17, wherein the diluent comprises a fluorinated glyme.

20. The electrolyte of claim 17, wherein the fluorinated glyme is 1,2-(1,1,2,2-tetrafluoroethoxy)-ethane (TFE).

21. The electrolyte of claim 20, wherein the salt comprises lithium bis(fluorosulfonyl)imide.

22. The electrolyte of claim 1, wherein the concentration of the salt is less than about 3M.

23. The electrolyte of claim 22, wherein, in the solvent: diluent volumetric percentage ratio, the solvent is at least 50% and the diluent is no more than 50%.

24. The electrolyte of claim 22, wherein, in the solvent: diluent volumetric percentage ratio, the solvent is at least 60% and the diluent is no more than 40%.

25. The electrolyte of claim 24, wherein the salt comprises lithium bis(fluoro-sulfonyl)imide.

26. The electrolyte of claim 1, wherein the salt comprises an alkali-metal salt.

27. The electrolyte of claim 26, wherein the salt comprises a perfluorinated sulfonimide salt.

28. The electrolyte of claim 27, wherein the perfluorinated sulfonimide salt comprises a lithium-based perfluorinated sulfonimide salt.

29. The electrolyte of claim 28, wherein the lithium-based perfluorinated sulfonimide salt comprises lithium bis(fluorosulfonyl)imide.

* * * * *